United States Patent [19]

Vayssie et al.

[11] Patent Number: 5,073,174
[45] Date of Patent: Dec. 17, 1991

[54] DYEING PROCESS EMPLOYING INDOLE DYES AND OXIDATION DYE PRECURSORS AND DYEING AGENTS EMPLOYED

[75] Inventors: Charles Vayssie, Villepinte; Daniel Bauer, Le Raincy; Francoise Richard, Montreuil; Alex Junino, Livry-Gargan, all of France

[73] Assignee: L'Oreal, Paris, France

[21] Appl. No.: 554,873

[22] Filed: Jul. 20, 1990

[30] Foreign Application Priority Data

Jul. 21, 1989 [FR] France ................. 89 09836

[51] Int. Cl.$^5$ .............................. A61K 7/13
[52] U.S. Cl. .......................... 8/406; 8/408; 8/409; 8/410; 8/415; 8/416; 8/423; 8/429
[58] Field of Search ............ 8/406, 408, 409, 410, 8/415, 416, 423, 429

[56] References Cited

U.S. PATENT DOCUMENTS 4,888,027 12/1989 Grollier et al. ............... 8/423

FOREIGN PATENT DOCUMENTS 0350385 10/1990 European Pat. Off. .
2613221 1/1989 France .
2207443 7/1988 United Kingdom .

Primary Examiner—Paul Lieberman
Assistant Examiner—William S. Parks
Attorney, Agent, or Firm—Cushman, Darby & Cushman

[57] ABSTRACT

A process for dyeing keratinous fibers comprises a two-step operation in which in the first step the fibers are contacted with an indole dye in a medium suitable for dyeing the fibers, the medium being free from any oxidation catalyst and oxidation catalyst. Thereafter, in the second step the fibers are contacted with a para type oxidation dye precursor in a medium which is also suitable for dyeing the fibers and is free from any oxidation catalyst and oxidation agent. A multi-compartment kit housing the indole dye and para type oxidation dye precursor is also provided.

19 Claims, No Drawings

DYEING PROCESS EMPLOYING INDOLE DYES AND OXIDATION DYE PRECURSORS AND DYEING AGENTS EMPLOYED

The present invention relates to a new process for dyeing keratinous fibres, more especially human keratinous fibres such as the hair, with an indole dye and an oxidation dye precursor.

The colours of hair dyed with compositions containing 5,6-dihydroxyindole differ according to the original colour, the nature of the hair and the method of application. The result obtained may be considered to be too light or too drab. It is hence advantageous to be able to vary the hue of this coloration, for example by the application of a second composition, either immediately after the first application or after a certain lapse of time which can range up to several days. It is also desirable to be able to effect this variation either locally or over the whole head of hair.

The inventors found, surprisingly, that by performing the application, in a first stage of a composition containing an indole dye without using an oxidizing agent other than the air, and in the second stage of a composition containing a para type oxidation dye precursor, there was a deepening of the colour and not a simple juxtaposition of the colours obtained with the said dyes taken individually.

Moreover, the inventors also found that the colorations thereby obtained were much warmer than the individual colorations obtained either with the indole dye alone or with the oxidation dye precursors alone.

This process does not employ the oxidation catalysts used in pre- or post-treatment. Apart from aerial oxygen, hydrogen peroxide can optionally be used in the second stage.

The subject of the invention is hence a new dyeing process employing an indole dye in a first step, and a para type oxidation dye precursor in a second step.

Other subjects of the invention will become apparent on reading the description and the examples which follow.

The process according to the invention, intended for the dyeing of keratinous fibres and especially human keratinous fibres such as the hair is characterized in that there is applied on these fibres:

in a first step, a composition (A) containing, in a medium suitable for dyeing and free from all oxidizing agents, at least one indole dye corresponding to the formula:

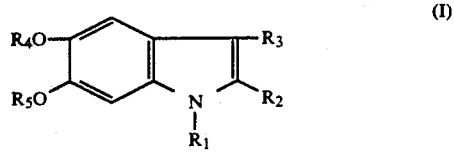

in which:

$R_1$ represents a hydrogen atom, a lower alkyl group or a group $-SiR_6R_7R_8$;

$R_2$ and $R_3$, which may be identical or different, represent a hydrogen atom or alternatively a lower alkyl group, a carboxyl group, a (lower alkoxy)carbonyl group or a group $-COOSiR_6R_7R_8$;

$R_4$ and $R_5$, which may be identical or different, represent a hydrogen atom, a linear or branched $C_1-C_{20}$ alkyl group, a formyl group, a linear or branched $C_2-C_{20}$ acyl group, a linear or branched $C_3-C_{20}$ alkenoyl group, a group $-SiR_6R_7R_8$, a group $-P(O)(OR_9)_2$, or a group $-SO_2OR_9$, or alternatively $R_4$ and $R_5$, together with the oxygen atoms to which they are attached, form a ring optionally containing a carbonyl group, a methylene group, a thiocarbonyl group or a group: $<P(O)OR_9$, or alternatively $<CR_{10}R_{11}$; and $R_9$ and $R_{10}$ represent a hydrogen atom or a lower alkyl group, $R_{11}$ representing a lower alkoxy group or a mono- or dialkylamino group, $R_6$, $R_7$ and $R_8$, which may be identical or different, representing linear or branched lower alkyl groups;

and the addition salts with inorganic or organic acids as well as the corresponding alkali metal, alkaline earth metal or amine salts; and in a second step, there is applied a composition (B) containing, in a medium suitable for dyeing, at least one para oxidation dye precursor selected from para-phenylenediamines, para-aminophenols and heterocyclic para bases derived from pyridine or from pyrimidine, and/or at least one "rapid" oxidation dye selected from trihydroxylated derivatives of benzene, diaminohydroxybenzenes, aminodihydroxybenzenes, substituted aminohydroxybenzenes, triaminobenzenes, substituted 1,2-dihydroxybenzenes, brazilin, haematoxylin and alkanet extract.

This second composition is optionally mixed at the time of use with a hydrogen peroxide solution.

According to the invention, the first stage and the second stage of the process may be separated by a rinse. When the treated fibres are rinsed after the application of the composition (A), it is possible, if desired, to dry the hair before the application of the second composition containing the oxidation dye precursors.

Preferred indole dyes corresponding to the formula (I) are selected from 5,6-dihydroxyindole, 2-methyl-5,6-dihydroxyindole, 5-methoxy-6-hydroxyindole, (5 or 6)-acetoxy-(6 or 5)-hydroxyindole, 2-carboxy-5,6-dihydroxyindole, 3-methyl-5,6-dihydroxyindole, 2,3-dimethyl-5,6-dihydroxyindole and their salts.

5,6-Dihydroxyindole is especially preferred; it is used as it is or in one of its protected forms such as, for example, the diacetate.

The para dye precursors are selected from the compounds corresponding to the formula:

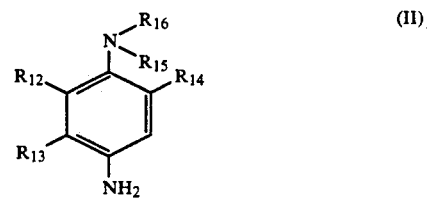

in which:

$R_{12}$, $R_{13}$ and $R_{14}$, which may be identical or different, denote a hydrogen or halogen atom, a lower alkyl radical or a lower alkoxy radical;

$R_{15}$ and $R_{16}$, which may be identical or different, denote a hydrogen atom or a lower alkyl, lower hydroxyalkyl, lower alkoxyalkyl, lower carbamylalkyl, lower sulphoalkyl, lower mesylaminoalkyl, lower acetylaminoalkyl, lower ureidoalkyl, lower carbethoxyaminoalkyl, lower piperidinoalkyl or lower morpholinoalkyl group, or alternatively $R_{15}$ and $R_{16}$, together with the nitrogen atom to which they are attached, form a piperidino or morpholino heterocycle, with the proviso that $R_{12}$ and $R_{14}$ represent a hydrogen atom when $R_{15}$ and $R_{16}$ do not represent a hydrogen atom;

as well as their addition salts with an acid, such as hydrochlorides, hydrobromides and sulphates.

In the abovementioned formulae, a lower alkyl or alkoxy radical denotes a radical having 1 to 6 carbon atoms.

Among especially preferred compounds of the formula (II), p-phenylenediamine, p-toluenediamine, methoxy-para-phenylenediamine, chloro-para-phenylenediamine, 2,6-dimethyl-p-phenylenediamine, 2,5-dimethylpara-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-bis($\beta$-hydroxyethyl)-para-phenylenediamine, 3-methyl-4-amino-N,N-bis ($\beta$-hydroxyethyl)aniline, 3-chloro-4-amino-N,N-bis($\beta$-hydroxyethyl)aniline, 4-amino-N-ethyl-N-(carbamylmethyl)aniline, 3-methyl-4-amino-N-ethyl-N-(carbamylmethyl)aniline, 4-amino-N-ethyl-N-($\beta$-piperidinoethyl)aniline, 3-methyl-4-amino-N-ethyl-N-($\beta$-piperidinoethyl)aniline, 4-amino-N-ethyl-N-($\beta$-morpholinoethyl)aniline, 3-methyl-4-amino-N-ethyl-N-($\beta$-morpholinoethyl)aniline, 4-amino-N-ethyl-N-($\beta$-acetylaminoethyl)aniline, 4-amino-N-($\beta$-methoxyethyl)aniline, 3-methyl-4-amino-N-ethyl-N-($\beta$-acetylaminoethyl)aniline, 4-amino-N-ethyl-N-($\beta$-mesylaminoethyl)aniline, 3-methyl-4-amino-N-ethyl-N-($\beta$-mesylaminoethyl)aniline, 4-amino-N-ethyl-N-($\beta$-sulphoethyl)aniline, 3-methyl-4-amino-N-ethyl-N-($\beta$-sulphoethyl)aniline, N-(4-aminophenyl)morpholine, N-(4-aminophenyl)piperidine, 2,3-dimethyl-p-phenylenediamine, isopropyl-p-phenylenediamine and their salts may be mentioned.

Among para-aminophenols, para-aminophenol, N-methyl-p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol,2-($\beta$-hydroxyethyl)-4-aminophenol, 2-methoxy-4-aminophenol and 3-methoxy-4-aminophenol may be mentioned.

The heterocyclic para oxidation dye precursors are derived from pyridine, such as 2,5-diaminopyridine and 2-hydroxy-5-aminopyridine, and those derived from pyrimidine consist, in particular, of tetraaminopyrimidine.

The so-called "rapid" oxidation dyes are selected from 1,2,4-trihydroxybenzene, 1,2,4-trihydroxy-5-($C_1$-$C_6$-alkyl) benzene, 4-aminoresorcinol, 1,2,3-trihydroxybenzene, 4-methyl-1,2-dihydroxybenzene, 2-amino-1,4-dihydroxybenzene, 2-amino-4-methoxyphenol, 2,4-diaminophenol, 3-methoxy-1,2-dihydroxybenzene, 1,4-dihydroxy-2-(N,N-diethylamino)benzene, 2,5-diamino-4-methoxy-1-hydroxybenzene, 4,6-dimethoxy-3-amino-1-hydroxybenzene, 2,6-dimethyl-4-[N-(p-hydroxyphenyl)amino]-1-hydroxybenzene, 1,5-diamino-2-methyl-4-[N-(p-hydroxyphenyl)amino]benzene and their salts.

The composition (B) can contain, in addition, a coupler selected from phenols, diphenols, m-phenylenediamines, m-aminophenols, hydroxynaphthalenes and heterocyclic couplers, in proportions not exceeding 3% by weight relative to the total weight of the composition.

The indole dye is used in the composition (A) according to the invention in proportions of between 0.1 and 5% by weight, and preferably between 0.2 and 2% by weight, relative to the total weight of the composition.

The para type dye precursors or "rapid" oxidation dyes are used in the composition (B) according to the invention in proportions of between 0.05 and 3% by weight, and especially between 0.1 and 2% by weight, relative to the total weight of the composition.

The pH of the composition (A) containing the indole dye is between 4 and 11, and preferably between 6 and 10.

The pH of the composition (B) containing the para type dye precursor and/or the "rapid" oxidation dye is between 7 and 12, and preferably 8 and 11.

The pH values are adjusted to the desired reading by means of alkalinizing or acidifying agents which are known per se and cosmetically acceptable when the compositions are intended for application on human hair.

These compositions can assume various forms, such as gels and more or less thickened lotions; they may be packaged as an aerosol, especially for dispensing in the form of a mousse.

The aqueous medium can contain, in addition, solvents generally present in proportions which can range up to 30% relative to the total weight of the composition, and selected from lower alcohols such as ethyl alcohol, propyl or isopropyl alcohol, tert-butyl alcohol; glycols such as ethylene glycol, propylene glycol; glycol ethers such as ethylene glycol monomethyl, monoethyl and monobutyl ethers, ethylene glycol monoethyl ether acetate, propylene glycol and dipropylene glycol monomethyl ethers; and methyl lactate.

Especially preferred solvents consist of ethyl alcohol and propylene glycol.

These compositions can also contain adjuvants well known in hair dyeing, such as antioxidant agents, thickening agents and conditioning agents; they can also contain surfactants, as well as silicones, in particular volatile silicones.

The thickening agents are selected from sodium alginate, gum arabic, guar or carob gum, heterobiopolysaccharides such as xanthan gum, cellulose derivatives such as methylcellulose, hydroxyethylcellulose, hydroxymethylcellulose, hydroxypropylcellulose and carboxymethylcellulose, and various polymers having thickening functions, such as acrylic acid derivatives. Inorganic thickening agents such as bentonite may also be used.

These thickening agents are preferably present in proportions of between 0.1 and 5% by weight, and especially between 0.5 and 3% by weight, relative to the total weight of the composition.

The process is carried out by applying the composition (A) on the fibres in a first stage and maintaining it in contact with the fibres for an exposure time of 1 to 60 minutes, and preferably 2 to 30 minutes, optionally followed by a rinse, a wash and drying. This application may be repeated.

It is followed by the application of the composition (B), which is maintained in contact with the fibres for a period of 1 to 60 minutes, preferably 1 to 20 minutes. The fibres are then rinsed, optionally washed with shampoo and dried.

The application of the composition (B) can take place immediately or after a lapse of time varying from a few minutes to several days.

The subject of the invention is also an agent for dyeing keratinous fibres, especially human keratinous fibres such as the hair, characterized in that it comprises two components, the first component consisting of a composition (A) containing at least one indole dye of the formula (I) as defined above in a medium suitable for dyeing, and the second component consisting of a composition (B) containing at least one para type oxidation dye precursor and/or one "rapid" oxidation dye as defined above in a medium suitable for dyeing.

This dyeing agent may be stored in a multicompartment device or dyeing kit, the different components being stored in separate compartments.

The examples which follow are intended as an illustration of the invention, no limitation of the latter being, however, implied.

EXAMPLE 1

The following compositions ($A_1$) and ($B_1$) are prepared:

| Composition ($A_1$): | | |
|---|---|---|
| 5,6-Dihydroxyindole | | 1.0 g |
| Ethanol | | 10.0 g |
| Sodium lauryl ether sulphate | | 1.0 g |
| pH 8.5 | | |
| Water | | qs 100.0 g |

This composition is applied for 10 minutes at room temperature on natural grey hair which is 90% white. The hair is then washed with shampoo and thereafter rinsed and dried. It is dyed dark blonde.

| Composition ($B_1$): | | |
|---|---|---|
| para-Aminophenol | | 1.0 g |
| Ethanol | | 12.0 g |
| Hydroxyethylcellulose sold by the company AQUALON under the name NATROSOL 250 HHR | | 1.5 g |
| Sodium hydroxide qs | pH 9.5 | |
| Water | | qs 100.0 g |

At the time of use, an equal volume of 6% hydrogen peroxide is added. This composition is applied on the hair pretreated with ($A_1$) for 3 minutes at room temperature. The hair is then rinsed and dried. It is dyed dark-auburn chestnut brown.

EXAMPLE 2

The composition ($A_1$) described in Example 1 is applied under the same conditions, and the following composition ($B_2$) is then applied:

| N,N-Bis($\beta$-hydroxyethyl)-para-phenylenediamine | | 1.0 g |
|---|---|---|
| Ethylene glycol monobutyl ether | | 15.0 g |
| Sodium lauryl ether sulphate containing 2 moles of ethylene oxide sold by the company LEVER under the name SACTIPON 85033 | | 3.5 g |
| Sodium hydroxide qs | pH 9.5 | |
| Water | | qs 100.0 g |

This composition is mixed at the time of use with an equal volume of 6% hydrogen peroxide. After 3 minutes' exposure, the hair is rinsed and dried. It is dyed chestnut brown.

EXAMPLE 3

The procedure is as in Example 1, using a composition ($B_3$) corresponding to ($B_1$) but which contains 1% of N-methyl-para-aminophenol in place of para-aminophenol. The hair is dyed dark-auburn coppery chestnut brown.

EXAMPLE 4

The procedure is as in Example 2, using a composition ($B_4$) which contains 2-methyl-4-aminophenol in place of N,N-bis($\beta$-hydroxyethyl)-para-phenylenediamine. A coppery golden light chestnut brown colour is obtained.

EXAMPLE 5

The procedure is as in Example 1, using a composition ($B_5$) containing 1% of para-phenylenediamine in place of para-aminophenol. A dark chestnut brown colour is obtained.

EXAMPLE 6

The procedure is as Example 5, except that 0.12% of para-phenylenediamine is used. A golden light chestnut brown colour is obtained.

EXAMPLE 7

The composition ($A_1$) described in Example 1 is applied under the same conditions, and the following composition ($B_7$) is then applied:

| para-Phenylenediamine | | 1.0 g |
|---|---|---|
| Ethanol | | 12.0 g |
| Hydroxyethylcellulose | | 1.5 g |
| Sodium hydroxide qs | pH 9.5 | |
| Water | | qs 100.0 g |

This composition is applied on hair dyed with the composition ($A_1$). It is left in place for 5 minutes and the hair is then rinsed and dried; it is dyed a golden dark blonde colour.

EXAMPLE 8

Grey locks which are 90% white are dyed with the composition ($A_1$) containing 5,6-dihydroxyindole under the conditions described above After drying, a lock dyed dark blonde is thereby obtained.

A composition ($B_8$) containing 1% by weight of 2,5-diaminopyridine in water to which an equal weight of 6% hydrogen peroxide solution has been added (pH of the mixture: 7.3) is applied on this lock for 3 minutes. After rinsing and drying, the lock has a stronger iridescent slightly dark-auburn tint.

EXAMPLE 9

By application of a 0.5% solution of 2-methyl-5,6-dihydroxyindole, pH 10, on locks of grey hair, and after 10 minutes' exposure followed by rinsing and drying, ashen light blonde locks are obtained.

If, in a second stage, a solution ($B_9$) similar to the composition ($B_1$) but containing 2% of para-aminophenol is applied, a lock dyed golden blonde with red glints is obtained.

EXAMPLE 10

Locks of grey hair which is 90% white are treated with a 0.5% solution of 5,6-dihydroxyindole, pH 9, for 15 minutes. After rinsing and drying, locks dyed metallic blonde are obtained.

If a 0.5% aqueous-alcoholic solution of 1,2,4-trihydroxybenzene is then applied in the presence of 3% hydrogen peroxide (pH of the mixture approximately 7)

for 3 minutes, the locks obtained are iridescent ash blonde.

EXAMPLE 11

A 2.5% aqueous-alcoholic solution of 5-methoxy-6-hydroxyindole is prepared and adjusted to pH 9 with sodium hydroxide. This solution is applied for 10 minutes on grey hair which is 90% white. After rinsing and drying, the hair is dyed slightly ashen grey.

A mixture of equal parts of a 0.5% solution of N-($\beta$-methoxyethyl)-para-phenylenediamine adjusted to pH 10 and 6% hydrogen peroxide is then applied for 3 minutes. After rinsing and drying, the hair is dyed a deep-purple light chestnut brown.

EXAMPLE 12

A 2.5% solution of 5-hydroxy-6-methoxyindole in aqueous alcohol containing 30% of alcohol is prepared and adjusted to pH 9 with sodium hydroxide. 1% of sodium lauryl ether sulphate is then added.

Locks of natural grey hair containing 90% of white hair are treated using this solution (bath ratio: 5 g per 1 g of hair) for 10 minutes at room temperature. After rinsing and drying, very slightly ashen light grey hair is obtained.

A 0.5% aqueous solution of N-($\beta$-methoxyethyl)-para-phenylenediamine, adjusted to pH 10 by adding sodium hydroxide, which is mixed with an equal quantity of 6% hydrogen peroxide, is applied on a previously treated lock. The treatment is performed for 3 minutes with a bath ratio of 5 g per 1 g of hair. After rinsing, washing and drying, a slightly bluish dark grey lock is obtained.

EXAMPLE 13

Locks of grey hair which is 90% white are treated with a 1% solution of 5-acetoxy-6-hydroxyindole in aqueous alcohol containing 35% of alcohol, in the presence of 1% of sodium lauryl ether sulphate. The application is performed on the basis of 5 g per g of hair for 10 minutes.

After rinsing and drying, ashen light blonde hair is obtained.

In a second step, a mixture of equal parts of a 1% solution of N,N-bis($\beta$-hydroxyethyl)-para-phenylenediamine, pH 10, and "6 volumes" hydrogen peroxide is applied to the hair thus treated for 3 minutes on the basis of 5 g of mixture per g of hair.

After rinsing, washing with a shampoo and drying, dark grey hair with deep-purple glints is obtained.

What is claimed is:

1. A process for dyeing keratinous fibers comprising applying to said fibers, in a first step, a composition (A) containing, in a medium suitable for dyeing said fibers and free from any oxidation catalyst and oxidation agent, at least one indole dye having the formula

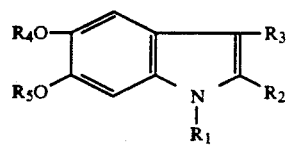

(I)

wherein
$R_1$ represents hydrogen, lower alkyl or $-SiR_6R_7R_8$, $R_2$ and $R_3$, each independently, represent hydrogen, lower alkyl, carboxyl, (lower alkoxy) carbonyl or $-COOSiR_6R_7R_8$, $R_4$ and $R_5$, each independently, represent hydrogen, linear or branched $C_1-C_{20}$ alkyl, formyl, linear or branched $C_2-C_{20}$ acyl, linear or branched $C_3-C_{20}$ alkenoyl, $-SiR_6R_7R_8$, $-P(O)(OR_9)_2$ or $-SO_2OR_9$, or $R_4$ and $R_5$ together with the oxygen atoms to which they are attached form a ring optionally containing a carbonyl group, a methylene group a thiocarbonyl group, a $<P(O)OR_9$ group or a $<CR_{10}R_{11}$ group, $R_9$ and $R_{10}$ represent hydrogen, or lower alkyl, $R_{11}$ represents lower alkoxy, monoalkylamino or dialkylamino, $R_6$, $R_7$ and $R_8$, each independently, represent linear or branched lower alkyl, and the acid addition salt with an inorganic or organic acid, and the corresponding alkali metal, alkaline earth metal or amine salt; said indole dye being present in said composition (A) in an amount ranging from 0.1 to 5 percent by weight; relative to the total weight of said composition (A), and in a second step, applying to said fibers a composition (B) containing, in a medium suitable for dyeing said fibers and free from any oxidation catalyst and oxidation agent, (i) at least one para oxidation dye precursor selected from the group consisting of a paraphenylenediamine, a paraaminophenol and a heterocyclic para base selected from the group consisting of a pyridine derivative and a pyrimidine derivative or (ii) at least one rapid oxidation dye selected from the group consisting a trihydroxylated benzene derivative, diaminohydroxybenzene, aminodihydroxybenzene, a substituted aminohydroxybenzene, triaminobenzene, a substituted 1,2-dihydroxybenzene, brazilin, haematoxylin and alkanet extract or both (i) and (ii), said para oxidation dye precursor or said rapid oxidation dye or both being present in said composition (B) in an amount ranging from 0.05 to 3 percent by weight relative to the total weight of said composition (B), said composition (B) optionally being mixed at the time of use with hydrogen peroxide.

2. Process according to claim 1, wherein a rinsing of the treated fibres is performed after application of the composition (A).

3. Process according to claim 2, wherein this rinsing is followed by a step of drying the hair before the application of the composition (B).

4. Process according to claim 1, wherein the indole dyes of the formula (I) are selected from 5,6-dihydroxyindole, 2-methyl-5,6-dihydroxyindole, 5-methoxy-6-hydroxyindole, (5 or 6)-acetoxy-(6 or 5)-hydroxyindole, 2-carboxy-5,6-dihydroxyindole, 3-methyl5,6-dihydroxyindole, 2,3-dimethyl-5,6-dihydroxyindole and their salts.

5. Process according to claim 1, wherein the paraphenylenediamines correspond to the formula (II):

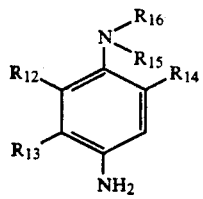

(II)

in which:

R$_{12}$, R$_{13}$ and R$_{14}$, which may be identical or different, denote a hydrogen atom or halogen atom, a lower alkyl radical or a lower alcoxy radical;

R$_{15}$ and R$_{16}$, which may be identical or different, denote a hydrogen atom or a lower alkyl, lower hydroxyalkyl, lower alkoxyalkyl, lower carbamylakyl, lower sulphoalkyl, lower mesylaminoalkyl, lower acetylaminoalkyl, lower ureidoalkyl, lower carbethoxyaminoalkyl, lower piperidinoalkyl or lower morpholinoalkyl group, or alternatively R$_{15}$ and R$_{16}$, together with the atom to which they are attached, form a piperidino or morpholino heterocycle, with the proviso that R$_{12}$ and R$_{14}$ represent a hydrogen atom when R$_{15}$ and R$_{16}$ do not represent a hydrogen atom; as well the corresponding salts.

6. Process according to claim 1, where the paraphenylenediamines are selected from the p-phenylenediamine, p-toluenediamine, methoxy-paraphenylenediamine, chloro-para-phenylenediamine, 2,6-dimethyl-p-phenylenediamine, 2,5-dimethyl-paraphenylenediamine, 2-methyl-5-methoxy-paraphenylenediamine, 2,6-dimethyl-5-methoxy-paraphenylenediamine, N,N-dimethyl-para-phenylenediamine, 3-methyl-4-amino-N,N-diethylaniline, N,N-bis(β-hydroxyethyl)-para-phenylenediamine, 3-methyl-4-amino-N,N-bis(β-hydroxyethyl)aniline, 3-chloro-4-amino-N,N-bis(β-hydroxymethyl)aniline, 4-amino-N-ethyl-N-(carbamylmethyl)aniline, 3-methyl-4-amino-N-ethyl-N-(carbamylmethyl)aniline, 4-amino-N-ethyl-N-(β-piperidinoethyl)aniline, 3-methyl-4-amino-N-ethyl-N-(β-piperidinoethyl)aniline, 4-amino-N-ethyl-N-(β-morpholinoethyl)aniline, 3-methyl-4-amino-N-ethyl-N-(β-morpholinoethyl)aniline, 4-amino-N-ethyl-N-(β-acetylaminoethyl)aniline, 4-amino-N-(β-methoxyethyl)aniline, 3-methyl-4-amino-N-ethyl-N-(β-acetylaminoethyl)aniline, 4-amino-N-ethyl-N-(β-mesylaminoethyl)aniline, 3-methyl-4-amino-N-ethyl-N-(β-mesylaminoethyl)aniline, 4-amino-N-ethyl-N-(β-sulphoethyl)aniline, 3-methyl-4-amino-N-ethyl-N-(β-sulphoethyl)aniline, N-(4-aminophenyl)morpholine, N-(4aminophenyl)-piperidine, 2,3-dimethyl-p-phenylenediamine, isopropyl-p-phenylenediamine and their salts.

7. Process according to claim 1, wherein the paraaminophenols are selected from para-aminophenol, N-methyl-p-aminophenol, 2-methyl-4-aminophenol, 3-methyl-4-aminophenol, 2-chloro-4-aminophenol, 3-chloro-4-aminophenol, 2,6-dimethyl-4-amino-phenol, 3,5-dimethyl-4-aminophenol, 2,3-dimethyl-4-aminophenol, 2,5-dimethyl-4-aminophenol,2-hydroxymethyl-4-aminophenol, 2-(β-hydroxyethyl)-4-aminophenol, 2-methoxy-4-aminophenol and 3-methoxy-4-aminophenol.

8. Process according to claim 1, wherein the heterocyclic para oxidation dyes are selected from 2,5-diaminopyridine, 2-hydroxy-5-aminopyridine and tetraaminoprimidine.

9. Process according to claim 1, wherein the "rapid" oxidation dye is selected from 1,2,4-trihydroxybenzene, 1,2,4-trihydroxy-5-(C$^1$-C$_6$alkyl)benzene, 4-aminoresorcinol, 1,2,3-trihydroxybenzene, 4-methyl-1,2-dihydroxybenzene,2-amino-1,4-dihydroxybenzene, 2-amino-4-methoxyphenol, 2,4-diamino-phenol, 3-methoxy-1,2-dihydroxybenzene, 1,4-dihydroxy-2-(N,N-diethylamino)benzene, 2,5-diamino-4-methoxy-1-hydroxybenzene, 4,6-dimethoxy-3-amino-1-hydroxybenzene, 2,6-dimethyl-4-[N-(p-hydroxyphenyl)amino]-1-hydroxy-benzene, 1,5-diamino-2-methyl-4-[N-(p-hydroxyphenyl)-amino]benzene and their salts.

10. Process according to claim 1, wherein the medium suitable for dyeing is an aqueous medium consisting of water or a water/solvent(s) mixture.

11. Process according to claim 1, wherein the pH of the composition (A) is between 4 and 11.

12. Process according to claim 1, wherein the pH of the composition (B) is between 7 and 12.

13. Process according to claim 1, wherein the composition (B) contains, in addition, a coupler in proportions not exceeding 3% by weight relative to the total weight of the composition.

14. Process according to claim 1, wherein the aqueous medium contains up to 30% of solvent selected from alcohols, glycols, glycol ethers and methyl lactate.

15. Process according to claim 1, wherein the compositions (A) and/or (B) are presented in the form of a lotion, thickened or other wise, a gel or an aerosol mousse.

16. Process according to claim 1, wherein the composition (A) applied in a first stage is maintained in contact with the air for a period of between 1 minute and 60 minutes.

17. Process according to claim 1, wherein the composition (B) is applied in the second stage on the fibres treated with the composition (A), either immediately after the application of the latter, or postponing the second stage for a lapse of time which can vary between a few minutes and several days.

18. Process according to claim 17, wherein the composition (B) is maintained in contact with the hair for a period of between 1 minute and 60 minutes.

19. A keratinous fiber multi-compartment kit comprising
a first compartment containing a composition (A) containing, in a medium suitable for dyeing said fiber and free from any oxidation catalyst and oxidation agent, at least one indole dye having the formula

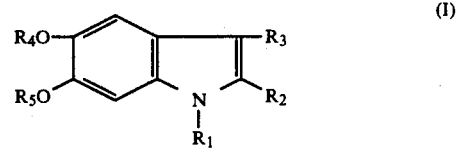

(I)

wherein

R$_1$ represents hydrogen, lower alkyl or —SiR$_6$R$_7$R$_8$,

R$_2$ and R$_3$, each independently, represent hydrogen, lower alkyl, carboxyl, (lower alkoxy) carbonyl or —COOSiR$_6$R$_7$R$_8$, R$_4$ and R$_5$, each independently, represent hydrogen, linear or branched C$_1$-C$_{20}$ alkyl, formyl, linear or branched C$_2$-C$_{20}$ acyl, linear or branched C$_3$-C$_{20}$ alkenoyl, —SiR$_6$R$_7$R$_8$, —P(O)(OR$_9$)$_2$ or —SO- $_2OR_9$, or $R_4$ and $R_5$ together with the oxygen atoms to which they are attached form a ring optionally containing a carbonyl group, a methylene group a thiocarbonyl group, a $<P(O)OR_9$ group or a $<CR_{10}R_{11}$ group, $R_9$ and $R_{10}$ represent hydrogen, or lower alkyl, $R_{11}$ represents lower alkoxy, monoalkylamino or dialkylamino, $R_6$, $R_7$ and $R_8$, each independently, represent linear or branched lower alkyl, and the acid addition salt with an inorganic or organic acid, and the corresponding alkali metal, alkaline earth metal or amine salt; said indole dye being present in said composition (A) in an amount ranging from 0.1 to 5 percent by weight; relative to the total weight of said composition (A), and a second compartment containing a composition (B) containing, in a medium suitable for dyeing said fibers and free from any oxidation catalyst and oxidation agent, (i) at least one para oxidation dye precursor selected from the group consisting of a paraphenylenediamine, a paraaminophenol and a heterocyclic para base selected from the group consisting of a pyridine derivative and a pyrimidine derivative or (ii) at least one rapid oxidation dye selected from the group consisting a trihydroxylated benzene derivative, diaminohydroxybenzene, aminodihydroxybenzene, a substituted aminohydroxybenzene, triaminobenzene, a substituted 1,2-dihydroxybenzene, brazilin, haematoxylin and alkanet extract or both (i) and (ii), said para oxidation dye precursor or said rapid oxidation dye or both being present in said composition (B) in an amount ranging from 0.05 to 3 percent by weight relative to the total weight of said composition (B).

* * * * *